United States Patent [19]
Popoff et al.

[11] Patent Number: 5,804,378
[45] Date of Patent: *Sep. 8, 1998

[54] **NUCLEIC ACID SEQUENCES DERIVED FROM THE GENOME OF *SALMONELLA TYPHI*, AND THEIR USES, IN PARTICULAR FOR THE IN VITRO DIAGNOSIS OF THE PRESENCE OF BACTERIA OF THE SALMONELLA GENUS IN FOODSTUFFS**

[75] Inventors: Michel Yvan Popoff, Plaisir; Michel Dion, Paris, both of France

[73] Assignees: Institut Pasteur; Institut National de la Sante et de la Recherche Medicale (INSERM), both of Paris Cedex, France

[*] Notice: The term of this patent shall not extend beyond the expiration date of Pat. No. 5,618,666.

[21] Appl. No.: 476,678

[22] Filed: Jun. 7, 1995

Related U.S. Application Data

[63] Continuation of Ser. No. 961,702, Mar. 10, 1993, Pat. No. 5,618,666, filed as PCT/FR91/00564 on Jul. 11, 1991.

[30]    Foreign Application Priority Data

Jul. 11, 1990 [FR] France ................................ 90 08852

[51] Int. Cl.⁶ .............................. C12Q 1/68; C07H 21/04
[52] U.S. Cl. .......................... 435/6; 536/23.7; 536/24.32; 536/24.33
[58] Field of Search ............................. 435/6, 91.2, 810; 536/23.7, 24.32, 24.33

[56]        References Cited

U.S. PATENT DOCUMENTS

| 4,965,188 | 10/1990 | Mullis et al. ................................. 435/6 |
| 5,618,666 | 4/1997  | Popoff et al. ................................ 435/6 |
| 5,681,716 | 10/1997 | Popoff et al. ........................... 435/69.1 |

OTHER PUBLICATIONS

Miras et al. Res. Microbiol. (1995) 146 : 17–20.
Hermant et al. Molecular Microbiol. (1995) 17(4): 781–789.
Galan et al. J. Bacteriol (Jul. 1992) 174(13): 4338–4349.
Eichelberg et al. J. Bacteriol. (Aug. 1994) 176 (15): 4501–4510.
Galan et al., P.N.A.S. 86:6383–6387, Aug. 1989.
Mroczenski–Wildey et al., in "Invasion and Lysis of Hela Cell Monolayers by *Salmonella Typhi*: The Role of Liposaccharide" Academic Press, pp. 143–152, Feb. 1989.

*Primary Examiner*—Lisa B. Arthur
*Attorney, Agent, or Firm*—Oblon, Spivak, McClelland, Maier & Neustadt, P.C.

[57]         ABSTRACT

Nucleic sequences from the genome of Salmonella Typhi include all or part of the genetic information required for the in vitro infection of cultured HeLa cells by Salmonella bacteria. Polypeptides encoded by these nucleic sequences are also described, as is the use of said polypeptides and nucleic sequences for implementing methods of in vitro Salmonella detection in biological samples which are thought to contain it.

15 Claims, 1 Drawing Sheet

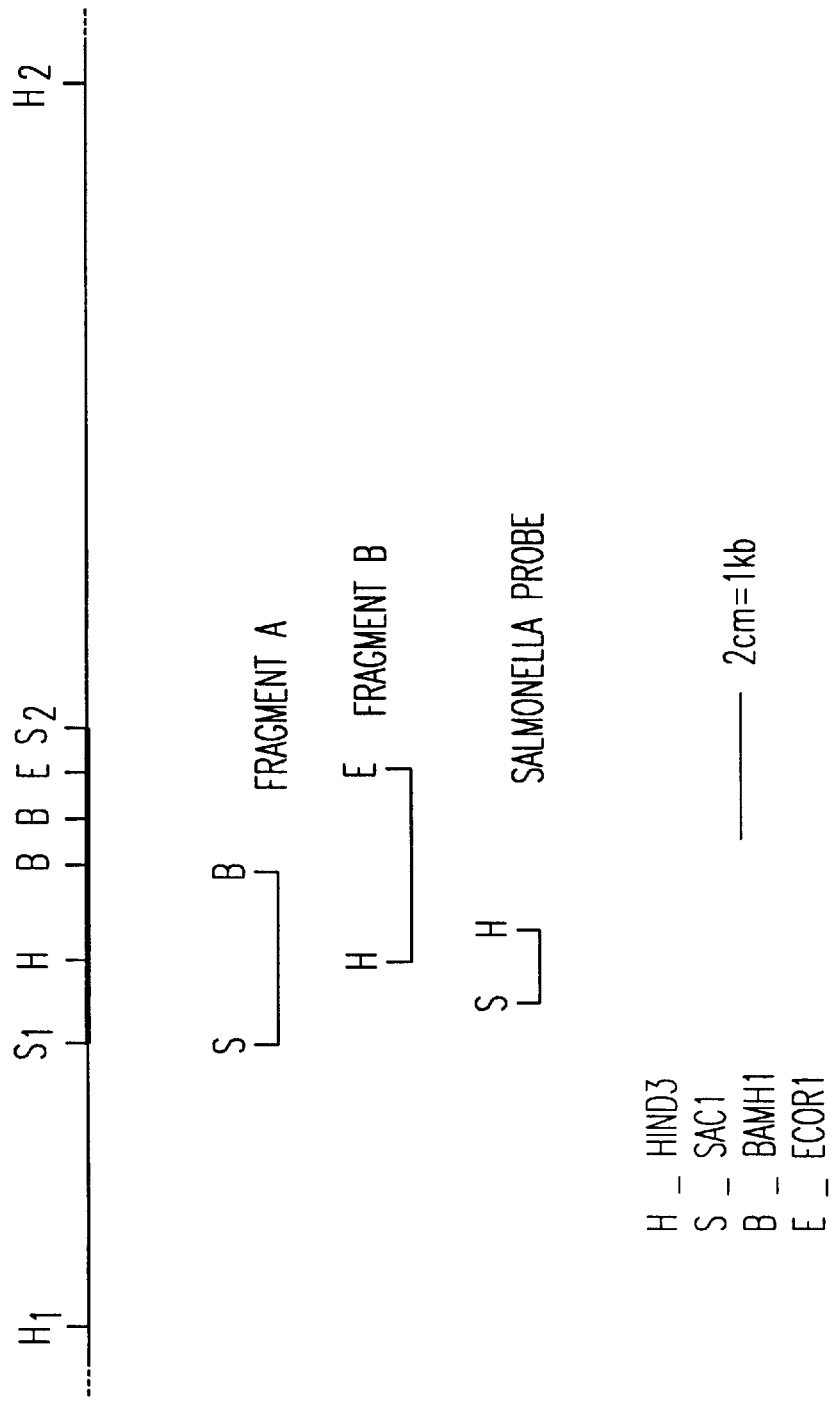

NUCLEIC ACID SEQUENCES DERIVED FROM THE GENOME OF *SALMONELLA TYPHI*, AND THEIR USES, IN PARTICULAR FOR THE IN VITRO DIAGNOSIS OF THE PRESENCE OF BACTERIA OF THE SALMONELLA GENUS IN FOODSTUFFS

This is a Continuation of application Ser. No. 07/961,702, filed on Mar. 10, 1993, now U.S. Pat. No. 5,618,666, which was filed under U.S.C. 371 as International Application No. PCT/FR91/00564, on Jul. 11, 1991.

BACKGROUND OF THE INVENTION

1. Field of the Invention

The subject of the present invention is nucleic acid sequences derived from the genome of Salmonella Typhi, and their use, in particular, for the in vitro diagnosis of the presence of bacteria of the Salmonella genus in a biological sample likely to contain them, and more particularly in foodstuffs.

2. Description of the Related Art

At present, foodstuffs are of growing importance. For social reasons, transformed foodstuffs, ready for consumption, continue to create an increasing demand on the part of the buyers. The result of this is that the sources of production and display of these products have been modified considerably during the last fifteen years (mass manufacture in specialised factories; marketing in packaged units, usually in a plastic wrapping).

For reasons of public health, the manufacturing technologies and the products themselves are subjected to stricter and stricter measures of health supervision. In the framework of bacteriological controls, the bacteria responsible for toxic infections of foodstuffs are investigated systematically, and among them priority is given to the Salmonella. Moreover, the health standards are very clear for this, bacterial genus: absence of Salmonella in 25 grams of product.

From the point of view of taxonomy, the Salmonella genus belongs to the family of the Enterobacteriaceae. This genus includes a single and unique species, *S.enterica*, which may be subdivided into seven sub-species. Within each of these sub-species, it is possible to identify a large number of serotypes with the aid of sera directed against the polysaccharide O antigens and the flagellar H antigens. In 1989, 2267 serotypes of Salmonella were known.

The Salmonella are entero-invasive bacteria, which are pathogenic for man and animals. Their pathogenic potency is linked to their capacity to invade the intestinal epithelium. This stage can be limited to the mucosal membranes in the case of a toxic infection for example, or be followed by systemic dissemination (the case of typhoid fever). The contamination of the host by Salmonella occurs by the mouth in the very great majority of cases. This explains why the Salmonella are systematically investigated in the context of bacteriological controls of biological samples.

The standard method of systematic investigation of Salmonella, recommended by the Association Francaise de Normalisation (AFNOR) comprises: the placing in culture of the product to be analysed in two different enrichment media, incubated at two different temperatures and isolated on two different selective media (this step is often preceded by a "revivification" step in a nutrient broth); subculturing of at least 6 colonies on media for rapid identification; finally, serological typing of the strain. Even though the AFNOR protocol must be scrupulously followed during an official expert investigation, it can be imagined that it is difficult to apply during systematic controls on account of the time needed to carry out the investigation (at least one week) and its cost.

Novel methods of investigation of Salmonella are based either on enzymatic assays or on the use of nucleic acid probes. It must be emphasized that in the two cases a culture step on a rich medium and a subculture in an enrichment medium are recommended, and even essential.

The immuno-enzymatic assays which use monoclonal antibodies are easy to implement, give results in four to six hours and are available at a reasonable price. Their great disadvantage lies in the fact that they often give false positive reactions and sometimes false negative reactions. The consequences of such false reactions are considerable in both cases: if a false positive reaction is produced, there will be seizure of the product and the initiation by the analytical laboratory of a process to isolate a Salmonella which does not exist: if a false negative reaction is produced, the product will be marketed with the risks which that entails for public health.

A recent study involving 250 strains of Salmonella and 75 bacterial strains not belonging to the Salmonella genus produced 17 false positive reactions and 2 false negative reactions (D'AOUST, J. Y. (1987): "Efficacy of the immunoenzymatic kit BIOENZABEAD for the screening of Salmonella spp. in foodstuffs", Microorganisms and Foodstuffs: Rapid Procedure, industrial control. Colloquium of the French Society of Microbiology, Paris). Since this study was performed on pure cultures, it can be imagined that the number of false reactions would have been much larger with poly-microbial products (microbial competition; risk of antigenic cross-reactions).

The nucleic acid probes are constituted by a genomic DNA fragment (FITTS, R. et al. (1983), "DNA-DNA Hybridization Assay For Detection of Salmonella spp". In Foods, Applied and Environmental Microbiology, 46, 1146–1151). They are reputed to be specific. Several kits exist on the market. In fact, it appears that these probes present two major disadvantages: their lack of specificity according to the results communicated by users(cross-reaction with the Citrobacter, for example) and their lack of sensitivity (threshold limit of detection: $10^5$ Salmonella: or according to some authors, 2.5 $\mu$g of DNA, i.e. about $10^7$ bacteria).

SUMMARY OF THE INVENTION

The subject of the present invention is precisely nucleic acid sequences which can be used as nucleic acid probes for the detection of Salmonella, these probes being completely specific for the Salmonella genus (no cross-reaction with other bacteria, in particular with the bacteria of the Citrobacter genus).

The subject of the invention is also the use of these nucleic acid probes in in vitro detection or assay methods for Salmonella which exhibit the following advantages:

—high sensitivity,
—rapid response; the results of the analysis may be known in 48 hours, and even in 24 hours,
—easy implementation, in particular without the use of a radioactive substance,
—reasonable cost.

Salmonella sub-species *enterica* serotype Typhi (bacterium designated as Typhi hereafter) is the agent of human typhoid fever. This bacterium is strictly pathogenic for man. As a result of contamination by mouth, Typhi will cross the intestinal barrier and reach the mesenteric ganglia owing to a genetic system which allows it to adhere to and penetrate into the epithelial cells of the intestinal mucosa. In the absence of an experimental model, this first step of infection is studied in vitro on HeLa cells in culture, since Typhi is capable of adhering to and penetrating into these cells.

The subject of the invention is precisely any nucleic acid sequence characterized in that it includes all or part of the genetic information necessary for the in vitro infective activity towards HeLa cells in culture manifested by the bacteria of the Salmonella genus.

BRIEF DESCRIPTION OF THE DRAWINGS

FIG. 1 depicts a restriction map of a nucleotide sequence of the invention which contains a sequence of 2 kb delimited two SacI sites designated as $S_1$ and $S_2$.

DESCRIPTION OF THE PREFERRED EMBODIMENTS

More precisely, the subject of the invention is any nucleic acid sequence such as that defined above which includes all or part of the sequence of 7.9 kb delimited by the two HindIII sites, designated as $H_1$ and $H_2$ on the restriction map of the said sequence shown in FIG. 1.

The nucleic acid sequences of the invention are more particularly those corresponding to the characteristics defined above and are derived from the genome of the Ty 2 strain of Typhi deposited with the Pasteur Institute Collection under No. CIP 55-35.

More particularly, the invention relates to any nucleic acid sequence derived from the genome of the Ty 2 strain mentioned above, this sequence containing all or part of the genetic information defined above and including all or part of the sequence of 2 kb delimited by the two SacI sites, designated as $S_1$ and $S_2$ on the restriction map shown in FIG. 1.

More generally, the invention relates to any nucleic acid sequence containing all or part of the genetic information necessary for the in vitro infective activity towards HeLa cells of the bacteria of the Salmonella genus, and which is capable of hybridizing with all or part of at least one of the nucleic acid sequences defined above under stringent conditions. These stringent conditions are the following: 65° C. for 18 hours in 6×SSC (1×SSC consists of 0.15M NaCl and 0.015M trisodium citrate at pH 7) in Denhardt medium (0.1% Ficoll; 0.1% polyvinyl-pyrrolidone; 0.1% bovine serum albumin).

The invention also relates to any nucleic acid sequence included in one of the nucleic acid sequences defined above, or capable of hybridizing with one of these sequences under the hybridization conditions defined above, and which can be used as probe for the implementation of an in vitro detection procedure for bacteria of the Salmonella genus, and more particularly for the pathogenic Salmonella such as Typhi, which are capable of adhering to and penetrating into the epithelial cells of the intestinal mucosa of the organism.

Advantageously, the nucleic acid probes of the invention are constituted of a succession of about 200 to 500 nucleotides.

For example, the subject of the invention is more particularly a nucleic acid probe characterized by the following nucleotide sequence (I; SEQ ID NO:1)

1
5'> CAATTACGCCCCGATTATTATATCTCCGGGCAGATGATACCCGAT
GGTAATGATAATATTGTACAGATCGAGATAGTTCGGGTTAAAGGT

TATCACCTGCTGCACCAGGAAAGCATTAAGTTGATAGAACACCAA

CCCGCTTCTCTCTTGCAAAACAAAATTGCGAATCTTTTGCTCAGA

TGTATTCCCGGACTTCGCTGGGACACAAAGCAAATTAGCGAGCTA

AATTCGATTGACAGTACCATGGTCTACTTACGCGGTAAGCATGAG

TTAAATCAATACACCCCCTATAGCTTACAGCAAGCGCTTAAATTG

CTGACTCAATGCGTTAATATGTCGCCAAACAGCATTGCGCCTTAC

TGTGCGCTGGCAGAATGCTACCTCAGCATGGCGCAAATGGGGATT

TTTGATAAACAAAACGCAATGATCAAAGCTAAAGAACATGCGATT

AAGGCGACAGAGCTGGACCACAATAATCCACAAGCTT$_{487}$ <3'

The invention also relates to any nucleic acid sequence included in one of the nucleic acid sequences defined above, or capable of hybridizing with one of these sequences under the conditions of hybridization defined above, and which can be used as nucleic acid primer for the gene amplification of one of the nucleic acid sequences of the invention.

Advantageously, the nucleic acid primers of the invention are constituted of a succession of about 10 to 30 nucleotides.

The procedures of gene amplification make a considerable contribution to the development of particularly sensitive in vitro diagnostic methods. Among such procedures of gene amplification, mention may be made of the PCR (Polymerase Chain Reaction) procedure such as described in the European patent applications No. 86/302.298.4 of Mar. 27, 1986 and No. 87/300.203.4 of Jan. 09, 1987, or also of the procedure called "Qβreplicase" described in Biotechnology, vol. 6, page 1197 (October 1988) and that resulting from the use of a RNA polymerase (T7RNA polymerase) described in the International patent application No. WO89/01050. These procedures make it possible to improve the sensitivity of detection of the nucleic acids of viruses or bacteria, and require the use of specific synthetic primers.

For example, the subject of the invention is more particularly the following nucleotide primers SS-1 (SEQ ID NO:3) and SS-2: (SEQ ID NO:4)

SS-1
5'>GGT CCA GCT CTG TCG CC<3'
SS-2
5'>CCG GGC AGA TGA TAC CC<3' which can be used for the amplification of the number of copies of the nucleic acid sequence defined by the nucleotides situated at the positions 26 and 469 of the nucleotide sequence (I; SEQ ID NO:1) of the invention.

Also included in the invention are the nucleic acid variants of the nucleic acid sequence (I; SEQ ID NO:1) or of the primers SS-1 (I; SEQ ID NO:3) and SS-2 (I; SEQ ID NO:4) defined above which bear certain localized mutations, to the extent to which these variant nucleic acids hybridize with the sequence (I; SEQ ID NO:1) or the nucleotide primers previously defined under the conditions of hybridization defined above in the description.

The subject of the invention is also any peptide or polypeptide corresponding to the nucleic acid sequence of the invention according to the universal genetic code.

For example, the invention relates more particularly to any polypeptide constituted by all or part of the following amino acid sequence (II; SEQ ID NO:2) this sequence corresponding to the nucleic acid sequence (I; SEQ ID NO:1) described above according to the universal genetic code:

GlnLeuArgProAspTyrTyrIleSerGlyGlnMetIleProAsp
GlyAsnAspAsnIleValGlnIleGluIleValArgValLysGly
TyrHisLeuLeuHisGlnGluSerIleLysLeuIleGluHisGln
ProAlaSerLeuLeuGlnAsnLysIleAlaAsnLeuLeuLeuArg
CysIleProGlyLeuArgTrpAspThrLysGlnIleSerGluLeu
AsnSerIleAspSerThrMetValTyrLeuArgGlyLysHisGlu
LeuAsnGlnTyrThrProTyrSerLeuGlnGlnAlaLeuLysLeu
LeuThrGlnCysValAsnMetSerProAsnSerIleAlaProTyr
CysAlaLeuAlaGluCysTyrLeuSerMetAlaGlnMetGlyIle
PheAspLysGlnAsnAlaMetIleLysAlaLysGluHisAlaIle
LysAlaThrGluLeuAspHisAsnAsnProGlnAla

It will be obvious, that any peptide sequence derived from the modification by substitution and/or by addition and/or deletion of one or more amino acids of a polypeptide of the invention, and more particularly of the peptide sequence (II; SEQ ID NO:2) described above or of a peptide sub-sequence derived from this latter is included in the framework of the present invention, provided that this modification does not impair the antigenic properties of the said polypeptide.

The invention also relates to the monoclonal or polyclonal antibodies which are capable of recognizing specifically the polypeptides of the invention, and of forming immunological complexes with these latter.

The polyclonal antibodies of the invention are obtained by immunization of an animal with the polypeptides of the invention, followed by the recovery of the antibodies formed.

The monoclonal antibodies of the invention are produced by any hybridoma capable of being formed by standard methods starting from the spleen cells of an animal, in particular mouse or rat, immunized with one of the purified polypeptides of the invention, on the one hand, and from the cells of a suitable myeloma cell line, on the other, and being selected by its capacity to produce monoclonal antibodies which recognize the polypeptide used initially for the immunization of the animals.

The invention also relates to an in vitro detection procedure (or diagnostic method) for the possible presence of bacteria of the Salmonella genus in a biological sample likely to contain them, characterized in that it comprises:
—where appropriate, the placing in culture of the sample,
—where appropriate, the amplification of the number of copies of the nucleic acid sequence to be detected with the aid of a nucleotide primer couple such as those defined above,
—the placing of the sample in contact with a nucleic acid probe such as defined above under the conditions of hybridization mentioned above,
—the possible detection of hybridization complexes formed between the above-mentioned probe and the nucleic acid sequence to be detected.

The step involving the placing of the biological sample in culture is advantageously carried out in the following manner: 25 g of the biological sample are placed in culture in 200 ml of nutrient broth in a 1 liter Erlenmeyer flask for 18 h at 37° C. with shaking.

The step involving the amplification of the nucleic acid sequence to be detected in the above-mentioned procedure advantageously comprises the following steps:
—a step involving the extraction of the nucleic acid to be detected belonging to the genome of the bacteria of the Salmonella genus possibly present in the biological sample and, where appropriate, a step involving treatment with the aid of a reverse transcriptase of the said nucleic acid if this latter is in the form of RNA,
—a cycle comprising the following steps:
   denaturation step of the double-stranded nucleic acid to be detected, which leads to the formation of a single-stranded nucleic acid; this step is advantageously performed at 94° C. for 120 seconds,
   step involving the reassociation of each of the strands of nucleic acid obtained during the preceding denaturation step by hybridization with at least one primer such as defined above by placing the above-mentioned strands in contact with at least one of the above-mentioned primer couples; this step is advantageously performed at 68° C. for 180 seconds,
   elongation step by formation, from the primers, of DNA strands complementary to the strands to which the primers are hybridized in the presence of a DNA polymerase and suitable quantities of the four different nucleoside triphosphates (dATP, dCTP, dGTP, dTTP), which leads to the formation of a larger number of double-stranded nucleic acids to be detected than at the preceding denaturation step; this step is advantageously performed at 72° C. for 90 seconds, this cycle being repeated a defined number of times (preferably between 20 and 30 times;) to obtain the said nucleic acid sequence to be detected possibly present in the biological sample in a proportion sufficient to make its detection possible.

Other methods for the amplification and/or detection of the nucleic acid sequences characteristic of the Salmonella using the probes and, where appropriate, the nucleotide primers described above, can be used in the framework of the present invention. For example, mention may be made of the method described in the International patent application WO 85/06700, or also that described in the European patent application No. 0357336.

The subject of the invention is also kits for the implementation of an in vitro detection procedure for bacteria of the Salmonella genus such as described above, these kits containing:
—where appropriate, a suitable medium for placing the biological sample in culture,
—at least one of the nucleotide primer couples described above,
—where appropriate, suitable reagents for the implementation of an amplification cycle, in particular a DNA (or RNA) polymerase, and suitable quantities of the 4 different nucleoside triphosphates,
—one (or more) nucleic acid probe(s) such as described above, possibly labelled and capable of hybridizing with the nucleic acid sequence(s) to be detected,
—reagents suitable for the implementation of the hybridization reaction between the above-mentioned probe(s) and the nucleic acid sequence(s) to be detected, —a reference biological fluid or tissue lacking nucleic acid sequences capable of hybridizing with the above-mentioned probe(s).

The subject of the invention is also an in vitro procedure for the detection of the possible presence of bacteria of the Salmonella genus in a biological sample likely to contain them, characterized in that it comprises:
—where appropriate, the placing of the biological sample in culture in the manner indicated above,
—where appropriate, the amplification of the number of copies of the nucleic acid sequence corresponding to the polypeptide to be detected according to the universal genetic code (this amplification being performed in accordance with the amplification cycle described above),
—the placing of the above-mentioned sample in contact with antibodies of the invention capable of forming an immunological complex with the polypeptide(s) to be detected,
—the possible detection of the immunological complexes formed between the said antibodies and the peptide sequence(s) to be detected.

The invention also relates to kits for the implementation of the detection procedure described above which contain:
—where appropriate, a medium suitable for placing the biological sample in culture,
—where appropriate, one of the primer couples described above and reagents suitable for the implementation of the amplification cycle, in particular the DNA(or RNA) polymerase and suitable quantities of the 4 different nucleoside triphosphates,
—polyclonal or monoclonal antibodies, which may be labelled, in particular radioactively or enzymatically, capable of forming immunological complexes with the peptide sequence(s) to be detected,
—reagents for the constitution of a medium to promote the occurrence of the immunological reaction between the antibodies and the above-mentioned peptide sequence(s),
—reagents making possible the detection of the immunological complexes formed as a result of the above-mentioned immunological reaction. Such reagents may also bear a label or be capable of being recognized in turn by a labelled reagent,
—a reference biological fluid or tissue lacking polypeptides capable of being recognized by the above-mentioned antibodies.

The invention also relates to a procedure for the preparation of the nucleic acid sequences described above, this procedure comprising the following steps:
—incubation of the genomic DNA isolated from a Salmonella Typhi bacterium by treatment with sodium hydroxide at pH 12.5,
—treatment of the DNA thus extracted with a suitable endonuclease,
—the cloning of the nucleic acids thus obtained in a suitable vector and the recovery of the desired nucleic acid with the aid of a suitable probe selected from those described above.

A particularly advantageous procedure for the preparation of the nucleic acid sequences of the invention comprises the following steps:
—the synthesis of DNA using the automated β-cyanoethyl phosphoramidite method described in Bioorganic Chemistry 4; 274–325 (1986),
—the cloning of the nucleic acids thus obtained in a suitable vector and the recovery of the nucleic acid by hybridization with a suitable probe selected from those described above.

Another procedure for the preparation of the nucleotide sequences of the invention comprises the following steps:
—the assembly of chemically synthesized oligonucleotides, provided at their ends with different restriction sites, the sequences of which are compatible with the amino acid sequence of the natural polypeptide according to the principle described in Proc. Natl. Acad. Sci. USA, 80; 7461–7465, (1983),
—the cloning of the nucleic acids thus obtained in a suitable vector and the recovery of the desired nucleic acid by means of hybridization with a suitable probe selected from those described above.

The subject of the invention is also any recombinant nucleic acid containing at least one nucleic acid sequence of the invention inserted into a nucleic acid heterologous with respect to the said nucleic acid sequence.

The invention relates more particularly to a recombinant nucleic acid such as defined above in which the nucleic acid sequence of the invention is preceded by a promoter (in particular an inducible promoter) under the control of which the transcription of the said sequence is capable of being effected and, where appropriate, followed by a sequence coding for the termination signals of transcription.

The invention relates to any recombinant vector used in particular for the cloning of a nucleic acid sequence of the invention and/or the expression of the polypeptide encoded in this sequence, and characterized in that it contains a recombinant nucleic acid such as defined above at one of its sites which is inessential for its replication.

As an example of the above-mentioned vector, mention may be made of plasmids, cosmids or phages.

The subject of the invention is also a procedure for the preparation of a polypeptide of the invention by transformation of a cell host with the aid of a recombinant vector of the type mentioned above, followed by the placing in culture of the cell host thus transformed and the recovery of the polypeptide from the culture medium.

Thus, the invention relates to any cell host transformed by a recombinant vector such as defined above which contains the regulatory elements making possible the expression of the nucleic acid sequence coding for a polypeptide according to the invention.

The present invention relates more particularly to a procedure for the preparation of a polypeptide of the invention comprising the following steps:
—where appropriate, the amplification of the amount of nucleotide sequences coding for the said polypeptide with the aid of two DNA primers selected such that one of these primers is identical with the first 10 to 30 nucleotides of the nucleotide sequence coding for the said polypeptide whereas the other primer is complementary to the last 10 to 30 nucleotides (or hybridizes with these last 10 to 30 nucleotides) of the said nucleotide sequence, or conversely such that one of these primers is identical with the last 10 to 30 nucleotides of the said sequence whereas the other primer is complementary to the first 10 to 30 nucleotides (or hybridizes with the first 10 to 30 nucleotides) of the said nucleotide sequence, followed by the introduction of the said sequences of nucleotides thus amplified into a suitable vector,
—the placing in culture in a suitable culture medium of a cell host previously transformed by a suitable vector containing a nucleic acid according to the invention containing the nucleotide sequence coding for the said polypeptide and
—the recovery of the polypeptide produced by the said transformed cell host from the above-mentioned culture medium.

The peptides according to the invention may be prepared by the standard procedures used in the field of peptide synthesis. This synthesis may be carried out in homogeneous solution or on a solid phase.

For example, recourse may be had to the synthetic procedure in homogeneous solution described by HOUBEN-WEYL in the monograph entitled "Methode der Organischen Chemie" (Methods in Organic Chemistry), edited by E. Wunsch, vol. 15-I and II., THIEME, Stuttgart 1974.

This method of synthesis consists of successively condensing the successive aminoacyl residues in the required order, or of condensing aminoacyl residues and fragments previously formed which already contain several amino acids in the correct order, or also of condensing several fragments thus prepared beforehand, it being understood that care will be taken to protect beforehand all of the reactive functions borne by these aminoacyl residues or fragments, with the exception of the amino function of the one and the carboxyl function of the other or vice-versa, which normally are required to participate in the formation of the peptide bonds, in particular after activation of the carboxyl function according to the methods well known in the synthesis of peptides. As a variant, it will also be possible to have recourse to coupling reactions making use of standard coupling reagents of the carbodiimide type, such as for example 1-ethyl-3-(3-dimethylaminopropyl)-carbodiimide.

When the aminoacyl residue used possesses an additional acidic function (in particular in the case of glutamic acid), such functions will be protected for example by means of t-butylester groups.

In the case of stepwise synthesis, the amino acids being added one at a time, the synthesis begins preferably with the condensation of the C-terminal amino acid with the amino acid which corresponds to the neighbouring aminoacyl residue in the desired sequence and so on, one after the other, until the N-terminal amino acid is reached. According to another preferred procedure of the invention, recourse is had to that described by R. D. MERRIFIELD in the article entitled "Solid phase peptide synthesis" (J. Am. Chem. Soc., 45, 2149–2154).

In order to manufacture a peptide chain according to the procedure of MERRIFIELD, recourse is had to a very porous polymeric resin, to which the first C-terminal amino acid of the chain is bound. This amino acid is bound to the resin by the intermediary of its carboxyl group and its amino function is protected, for example by means of the t-butoxycarbonyl group.

When the first C-terminal amino acid has thus been attached to the resin, the protecting group of the amine function is removed by washing the resin with an acid.

In the case in which the protecting group of the amine function is the t-butoxycarbonyl group, it may be removed by treatment of the resin with trifluoroacetic acid.

The second amino acid is then coupled to the deprotected amine function of the first, C-terminal amino acid to furnish the second aminoacyl residue of the desired sequence, counting from the C-terminus. Preferably, the carboxyl function of this second amino acid is activated, for example by means of dicyclohexylcarbodiimide and the amine function is protected, for example by means of t-butoxycarbonyl.

The first part of the desired peptide chain is thus produced, which contains two amino acids, and the terminal amine function of which is protected. As previously, the amine function is deprotected and it is then possible to proceed to the attachment of the third aminoacyl residue under conditions analogous to those for the addition of the second, penultimate C-terminal amino acid.

In this way, the amino acids which will constitute the peptide chain are added one after the other to the previously deprotected amino group of the portion of the peptide chain already formed which is attached to the resin.

When the desired peptide chain has been assembled in its entirety, the protecting groups of the different amino acids constituting the peptide chain are removed and the peptide is cleaved from the resin for example with the aid of hydrogen fluoride.

The invention will be further illustrated with the aid of examples contained in the detailed description which follows, the character of which is is no way limiting.

1. Isolation of the SacI fragment of 2 Kb.

The purpose of the present invention is the cloning of the adhesion-invasion system of Typhi.

The strain used is the Ty 2 strain of Typhi deposited with the PASTEUR INSTITUTE Collection under the reference number CIP 55-35.

Starting from a collection of 2000 independent mutants obtained by insertion of a transposon derived from Tn5 (MANOIL C. and BECKWITH J., 1985 TnPhoA: a transposon probe for protein export signals. Proc. Natl. Acad. Sci. USA, 82, 8129–8133) into the genome of the Typhi strain Ty 2, a mutant was obtained which was no longer invasive in the model of HeLa cells in culture. The procedure for the infection of the HeLa cells in culture by Typhi is the following: the HeLa cells are cultivated in a RPMI 1640 medium containing 10% fetal calf serum. These cells are infected with Typhi in a ratio of 100 bacteria per cell. After incubation for one hour at 37° C., the cells are washed with the culture medium, then replaced in culture in the presence of 100 µg/ml of gentamycin. The intracellular bacteria are detected after 24 h by the Giemsa stain.

After digestion of the genome of this mutant by means of the restriction endonuclease SacI, hybridization experiments on sheets of cellulose nitrate showed that the transposon had been inserted in a SacI fragment of 2 kilobases (Kb).

As the transposon used codes for resistance to kanamycin, it was possible to clone the SacI fragment of 2 Kb containing the transposon into the SacI site of the plasmid pUC18 (VIEIRA J. and MESSING J., 1982. The PUC plasmids, a M13mp7- derived system for insertion mutagenesis and sequencing with synthetic universal primers. Gene, 19, 259–268). It is by using this recombinant plasmid that the nucleic acid sequences forming the subject of the present invention were isolated.

The genomic DNA of the Ty 2 strain was digested by the endonuclease SacI and the products of this digestion were ligated into the SacI site of the cloning vector pUC18. This ligation mixture was used to transform the *Escherichia coli* strain HB101 (deposited with the PASTEUR INSTITUTE Collection under the reference number CIP 102400). The selection of the transformants was performed on nutritive gelose containing 100 µg/ml of ampicillin. After incubation for 24 hours in an incubator at 37° C., the transformants were subcultured on discs of cellulose nitrate deposited on nutritive gelose containing 100 µg/ml of ampicillin. In order to perform hybridization in situ, these discs were then treated with a denaturating solution (0.5M NaOH), then by a neutralizing solution (1M ammonium acetate, 0.02M NaOH). The DNA released and denatured by these treatments was bound to the cellulose nitrate discs by heating at 80° C. for 3 hours.

These cellulose nitrate discs thus prepared were hybridized with the SacI fragment of 2 kb containing the transposon and labelled with $^{32}P$. The hybridizations were performed at 65° C. for 24 hours in 6×SSC (1×SSC consists of 0.15M NaCl and 0.015M trisodium citrate at pH 7) in a Denhardt medium (0.1% Ficoll; 0.1% polyvinyl-pyrrolidone; 0.1% bovine serum albumin).

A E.coli clone HB101 was thus isolated containing a recombinant plasmid constituted of the cloning vector pUC18 in which was inserted a SacI fragment of 2 kb (delimited by the S1 and S2 sites on the restriction map of this fragment which is given in FIG. 1 as a line in bold type).

2. Genetic region associated with the SacI fragment of 2 kb.

The genomic DNA of the Ty 2 strain was digested by the endonuclease HindIII. The products of digestion, separated by means of electrophoresis on agarose gel, were transferred by capillarity to a cellulose nitrate sheet. They were then hybridized under the conditions described above with the SacI-BamHI fragment of 1.1 kb (fragment A in FIG. 1) or with the HindIII-EcoRI fragment of 1.3 kb (fragment B in FIG. 1) which are both contained within the SacI fragment of 2 kb.

It was observed that the SacI fragment of 2 kb was covered by two HindIII fragments of sizes equal to 2.3 kb and 5.6 kb, respectively, in the genome of the Typhi strain Ty 2 (i.e. a fragment of 7.9 kb delimited by the sites $H_1$ and $H_2$ on the enzymatic restriction map of this region which is given in FIG. 1).

3. Isolation of the probe for Salmonella.

The DNA of the recombinant plasmid containing the SacI fragment of 2 kb was digested with the endonucleases SacI and HindIII. This double digestion released a SacI-HindIII fragment of 487 base pairs, which was recloned between the restriction sites SacI and HindIII of the cloning vector pUC18.

This SacI-HindIII fragment of 487 base pairs is called hereafter "Probe for Salmonella" and corresponds to the nucleic acid sequence (I) defined above. The position of this SacI-HindIII fragment in the SacI fragment of 2 kb is shown in FIG. 1.

4. Control of the specificity of the probe for Salmonella.

In order to carry out this control, the strains used were cultivated for 24 hours at 37° C. in 200 µl of nutrient broth on microtitration plates with 96 wells. With the aid of a multi-point inoculator, these strains were replaced in culture for 5 hours at 37° C. on a nitrocellulose sheet deposited on a dish of nutrient gelose. The cellulose nitrate sheet is then treated and used for the in situ hybridization experiments.

In order to prepare the probe for Salmonella, the recombinant plasmid (pUC18 containing the SacI-HindIII fragment of 487 base pairs was digested by the endonucleases SacI and HindIII. After separation of the products of this digestion by means of electrophoresis on an agarose gel, the probe for Salmonella was purified by electro-elution. It was then labelled with $^{32}P$ by means of nick-translation.

The hybridization experiments were carried out at 65° C. in 6×SSC and a Denhardt medium for a reaction time of 18 hours. Under these experimental conditions, the specificity of the probe for Salmonella was checked with 768 bacterial strains which are divided between 384 strains not belonging to the Salmonella genus and 384 which do belong to the Salmonella genus and which represent the seven sub-species of the Salmonella genus. These 768 strains were obtained from the Collection and the Collaboration Center of the WHO of Reference and Research for the Salmonella and from the Collection of the National Center for the Salmonella.

None of the 384 strains not belonging to the Salmonella genus hybridized with the probe for Salmonella.

Of the 384 strains of Salmonella, 382 hybridized with the probe for Salmonella. One of the two strains which did not hybridize with the probe for Salmonella belongs to the Wedding serotype and the other to the Zuerich serotype. Both are reference strains for the serotype in question. In the case of these two strains, it was verified that they are not invasive in the model involving HeLa cells in culture and that they possess neither the homologous fragment of the probe for Salmonella nor even the SacI fragment of 2 kb.

5. Detection of Salmonella in the biological products after gene amplification.

In a biological product, it is not possible today to detect a bacterium belonging to a given species among several tens of millions of other bacteria. In order to be able to detect the presence of one Salmonella in a polymicrobial biological product with the aid of a nucleotide probe it is essential to perform:

an amplification of the number of bacteria to be detected by placing the sample to be analysed in culture;

an amplification of the number of copies of the target which it is desired to detect with the nucleotide probe by using the gene amplification procedure (or the "Polymerase Chain Reaction" procedure or PCR).

In the case of the Salmonella, the SacI-HindIII fragment of 487 base pairs (the probe for Salmonella) is specific for the Salmonella genus. If, starting from the biological sample to be analysed, the presence of this fragment is detected, it will be possible to deduce that the sample under study is contaminated by Salmonella.

5.1. Description of the two primers used for the PCR.

Starting from the nucleotide sequence (I) of the probe for Salmonella, two primers used to implement the gene amplification procedure were selected.

The sequences of 17 bases corresponding to the two primers, designated SS-1 (SEQ ID NO:3) and SS-2 (SEQ ID NO:4) in the above description, were used to amplify the number of copies of the probe for Salmonella.

5.2. Protocol used with the primers SS-1 (SEQ ID NO:3) and SS-2 (SEQ ID NO: 4) for the PCR.

This protocol was developed using the "gene amp" kit (trademark filed) sold by Perkin Elmer Cetus (catalogue number N 801-0055). The primers SS-1 (SEQ ID NO:3) and SS-2 (SEQ ID NO:4) were used at a final concentration of 200 pmole. The reaction mixture was prepared according to the manufacturer's instructions by using 10 µl of the solution containing the DNA to be amplified in a final volume of 50 µl. This mixture was subjected to 20 amplification cycles by using the "DNA thermal cycler" apparatus (trademark filed) sold by Perkin Elmer Cetus (catalogue number N801-0177) under the following conditions:

denaturation step at 94° C. for 120 seconds,
reassociation step at 68° C. for 180 seconds,
elongation step at 72° C. for 90 seconds.

The DNA thus amplified was visualized by means of electrophoresis (120 Volts for 30 minutes) in an agarose gel containing 2% of low melting agarose (BRL; catalogue number 5517) and % normal agarose (Sigma; catalogue number A-6877). After electrophoresis, the DNA was transferred to a cellulose nitrate sheet and hybridized with the probe for Salmonella labelled with $^{32}P$.

5.3 Specificity and sensitivity of the procedure

The LT2 strain of Salmonella serotype Typhimurium, deposited with the PASTEUR INSTITUTE Collection under the reference number CIP 60.62T and the HB101 strain of E.coli (CIP 102.400) were used to study the specificity and the sensitivity of the PCR procedure under the experimental conditions described above.

The solution containing the DNA to be amplified was prepared in the following manner:
1) the intact bacteria are suspended in 100 μl of distilled water;
2) the bacterial suspension is treated for 10 minutes at 100° C. in a microtube for centrifugation;
3) it is then centrifuged for 3 minutes at maximal speed in a microcentrifuge. Avoiding the centrifugation pellet, a 10 μl aliquot of this solution is taken for gene amplification.

When a pure culture of the LT2 strain of Salmonella serotype Typhimurium is used, the DNA of 10 or less than 10 bacteria can be detected in 10 μl of solution subjected to amplification. When the HB101 strain of E. coli is used, no amplification is detectable even when one works with the DNA corresponding to $10^6$ bacteria in 10 μl of solution subjected to amplification. When a mixture of the two bacterial strains is made, the DNA of 100 or less than 100 Salmonella is detected mixed with the DNA of $10^6$ E.coli HB101 in 10 μl of the solution subjected to amplification.

5.4. Detection assay of Salmonella in a sample reconstituted in the laboratory.

The sample used is a batch of ground meat intended for animal feed. It is very highly contaminated with aerobic or anaerobic, Gram positive or Gram negative bacteria. An approximate count made under the microscope makes it possible to estimate the total number of bacteria at $10^9$ per gram of ground meat. By counting on dishes of nutrient gelose, the number of aerobic bacteria growing in this medium was found to be equal to $10^8$ per gram of ground meat. This sample does not contain Salmonella: three analyses performed using the standard procedures of feedstuff bacteriology were found to be negative.

5.4.1. Preparation of the sample for analysis by means of PCR.

The sample was reconstituted by adding a variable number of Salmonella serotype Typhimurium (10, $10^2$, $10^3$, $10^4$, $10^5$ or $10^6$) to 25 g of ground meat. This reconstituted sample is placed in culture in 200 ml of trypto-casein soya broth in a 1 liter Erlenmeyer flask for 18 hours at 37° C. with shaking. 25 g of ground meat without Salmonella are treated in an identical manner.

The next day, the Erlenmeyer flask is left to stand for 15 minutes on the bench without shaking at room temperature so as to allow the larger pieces of debris to sediment. Then a 1 ml aliquot of broth is taken from the surface and transferred to a microtube for centrifugation and centrifugation is performed for 3 minutes at maximal speed in a microcentrifuge. The supernatant is completely removed with the aid of a Pasteur pipette. The bacterial pellet is completely resuspended in 100 μl of distilled water, then heated at 100° C. for 10 minutes. The tube is centrifuged again for 3 minutes at maximal speed. Avoiding the centrifugation pellet, a 10 μl aliquot of this solution is taken for the gene amplification under the conditions already described.

5.4.2. Specificity and sensitivity of the procedure.

If one starts with 25 grams of sample without Salmonella, it is not possible to detect any amplification of the DNA contained in 10 μl aliquots of the amplified solution. When one starts with 25 grams of sample containing $10^2$ or more than $10^2$ Salmonella, amplification of the DNA contained in the 10 μl of the amplified solution is detected.

We claim:

1. An isolated nucleic acid of at least 200 nucleotides in length which hybridizes to the sequence of the 7.9 kb fragment delimited by the two HindIII sites designated as H1 and H2 on the restriction map of the sequence shown in FIG. 1 wherein said sequence contains the sequence of SEQ ID NO:1 under the following conditions:

65° C. for 18 hours in 6×SSC in Denhardt medium, wherein said nucleic acid specifically detects pathogenic salmonella which adhere to and penetrate into epithelial cells of intestinal mucosa.

2. The nucleic acid according to claim 1, wherein said nucleic acid has a length of 200 to 500 nucleotides.

3. The nucleic acid according to claim 1, wherein said nucleic acid hybridizes to the sequence of 2 kb delimited by the two SacI sites designated as S1 and S2 on the restriction map of the sequence shown in FIG. 1.

4. The nucleic acid according to claim 1 having the following nucleotide sequence (I; SEQ ID NO:1):

5'> CAATTACGCCCCGATTATTATATCTCCGGGCAGATGATACCCGAT

GGTAATGATAATATTGTACAGATCGAGATAGTTCGGGTTAAAGGT

TATCACCTGCTGCACCAGGAAAGCATTAAGTTGATAGAACACCAA

CCCGCTTCTCTCTTGCAAAACAAAATTGCGAATCTTTTGCTCAGA

TGTATTCCCGGACTTCGCTGGGACACAAAGCAAATTAGCGAGCTA

AATTCGATTGACAGTACCATGGTCTACTTACGCGGTAAGCATGAG

TTAAATCAATACACCCCCTATAGCTTACAGCAAGCGCTTAAATTG

CTGACTCAATGCGTTAATATGTCGCCAAACAGCATTGCGCCTTAC

TGTGCGCTGGCAGAATGCTACCTCAGCATGGCGCAAATGGGGATT

TTTGATAAACAAAACGCAATGATCAAAGCTAAAGAACATGCGATT

AAGGCGACACAGAGCTGGACCACAATAATCCACAAGCTT$_{487}$ <3'

5. The nucleic acid according to claim 1, wherein said nucleic acid encodes the following amino acid sequence (II; SEQ ID NO:2) according to the universal genetic code:

| | | | | | | | | | | | | | | |
|---|---|---|---|---|---|---|---|---|---|---|---|---|---|---|
| Gln | Leu | Arg | Pro | Asp | Tyr | Tyr | Ile | Ser | Gly | Gln | Met | Ile | Pro | Asp |
| Gly | Asn | Asp | Asn | Ile | Val | Gln | Ile | Glu | Ile | Val | Arg | Val | Lys | Gly |
| Tyr | His | Leu | Leu | His | Gln | Glu | Ser | Ile | Lys | Leu | Ile | Glu | His | Gln |
| Pro | Ala | Ser | Leu | Leu | Gln | Asn | Lys | Ile | Ala | Asn | Leu | Leu | Leu | Arg |
| Cys | Ile | Pro | Gly | Leu | Arg | Trp | Asp | Tyr | Lys | Gln | Ile | Ser | Glu | Leu |
| Asn | Ser | Ile | Asp | Ser | Thr | Met | Val | Tyr | Leu | Arg | Gly | Lys | His | Glu |
| Leu | Asn | Gln | Tyr | Thr | Pro | Tyr | Ser | Leu | Gln | Gln | Ala | Leu | Lys | Leu |
| Leu | Thr | Gln | Cys | Val | Asn | Met | Ser | Pro | Asn | Ser | Ile | Ala | Pro | Tyr |
| Cys | Ala | Leu | Ala | Glu | Cys | Tyr | Leu | Ser | Met | Ala | Gln | Met | Gly | Ile |
| Phe | Asp | Lys | Gln | Asn | Ala | Met | Ile | Lys | Ala | Lys | Glu | His | Ala | Ile |
| Lys | Ala | Thr | Glu | Leu | Asp | His | Asn | Asn | Pro | Gln | Ala. | | | |

6. A primer consisting of a succession of about 10 to 30 nucleotides derived from a sequence according to claim 1.

7. A set of primers comprising primers according to claim 6, wherein said primers have the following nucleotide sequences (SEQ ID NOS:3 and 4 respectively):

5'>GGT CCA GCT CTG TCG CC<3' SS-1

5'>CCG GGC AGA TGA TAC CC<3' SS-2 and wherein said set of primers amplifies the region located between positions 26 and 469 of the nucleic acid of SEQ ID NO:1.

8. An isolated recombinant nucleic acid containing at least one nucleic acid sequence according to claim 1, inserted in a nucleic acid heterologous thereto.

9. A recombinant nucleic acid, wherein said nucleic acid comprises, in the 5' to 3' direction, a promoter, said nucleic acid according to claim 1, and, where appropriate, a transcription termination signal sequence, and wherein said promoter controls the transcription of said nucleic acid according to claim 1.

10. A recombinant vector, wherein said vector comprises a recombinant nucleic acid according to claim 8, inserted at a site inessential for replication of said vector.

11. The nucleic acid according to claim 1, wherein said nucleic acid sequence is derived from the genome of the Ty 2 strain of Salmonella Typhi.

12. An isolated nucleic acid, wherein said nucleic acid is the sequence of the 7.9 kb fragment containing the sequence of SEQ ID NO:1 delimited by the two HindIII sites, designated as $H_1$ and $H_2$ on the restriction map of said sequence shown in FIG. 1 or a part of said sequence comprising at least 200 nucleotides.

13. The isolated nucleic acid of claim 12 wherein said nucleic acid includes the sequence of 2 kb delimited by the two SacI sites, designated as $S_1$ and $S_2$ on the restriction map shown in FIG. 1 or a part of said sequence comprising at least 200 nucleotides.

14. A method of in vitro detection of bacteria of the Salmonella genus in a biological sample by detection of Salmonella nucleic acid sequences, said method comprising the steps of:

a) where appropriate, placing said sample in culture;

b) wherein appropriate, amplifying the copy number of the Salmonella nucleic acid sequences using a set of primers of a about 10 to 30 nucleotides derived from a nucleic acid according to claim 1;

c) contacting said sample with a nucleic acid according to claim 1, in stringent conditions of hybridization; and d) detecting the hybridization complexes formed between said nucleic acid according to claim 1 and said Salmonella nucleic acid sequences.

15. A kit in vitro detection of bacteria of the Salmonella genus, wherein said kit comprises:

a) where appropriate, a suitable medium for placing the biological sample in culture;

b) at least one set of primers of about 10 to 30 nucleotides derived from a nucleic acid according to claim 1;

c) where appropriate, reagents suitable for carrying out the amplification step;

d) one or several nucleic acids according to claim 1;

e) reagents suitable for carrying out the hybridization step between the nucleic acid of (d) and Salmonella nucleic acid sequences; and f)a reference biological fluid or tissue lacking nucleic acid sequences hybridizing with the nucleic acid of (d).

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 487 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..487

( x i ) SEQUENCE DESCRIPTION: SEQ ID NO: 1:

| CAA | TTA | CGC | CCC | GAT | TAT | TAT | ATC | TCC | GGG | CAG | ATG | ATA | CCC | GAT | GGT | 48 |
|---|---|---|---|---|---|---|---|---|---|---|---|---|---|---|---|---|
| Gln | Leu | Arg | Pro | Asp | Tyr | Tyr | Ile | Ser | Gly | Gln | Met | Ile | Pro | Asp | Gly | |
| 1 | | | | 5 | | | | | 10 | | | | | 15 | | |

| AAT | GAT | AAT | ATT | GTA | CAG | ATC | GAG | ATA | GTT | CGG | GTT | AAA | GGT | TAT | CAC | 96 |
|---|---|---|---|---|---|---|---|---|---|---|---|---|---|---|---|---|
| Asn | Asp | Asn | Ile | Val | Gln | Ile | Glu | Ile | Val | Arg | Val | Lys | Gly | Tyr | His | |
| | | | 20 | | | | 25 | | | | | 30 | | | | |

| | | | | | | | | | | | | | | | | |
|---|---|---|---|---|---|---|---|---|---|---|---|---|---|---|---|---|
| CTG | CTG | CAC | CAG | GAA | AGC | ATT | AAG | TTG | ATA | GAA | CAC | CAA | CCC | GCT | TCT | 144 |
| Leu | Leu | His | Gln | Glu | Ser | Ile | Lys | Leu | Ile | Glu | His | Gln | Pro | Ala | Ser | |
| | | 35 | | | | | 40 | | | | | 45 | | | | |
| CTC | TTG | CAA | AAC | AAA | ATT | GCG | AAT | CTT | TTG | CTC | AGA | TGT | ATT | CCC | GGA | 192 |
| Leu | Leu | Gln | Asn | Lys | Ile | Ala | Asn | Leu | Leu | Leu | Arg | Cys | Ile | Pro | Gly | |
| | 50 | | | | | 55 | | | | | 60 | | | | | |
| CTT | CGC | TGG | GAC | ACA | AAG | CAA | ATT | AGC | GAG | CTA | AAT | TCG | ATT | GAC | AGT | 240 |
| Leu | Arg | Trp | Asp | Thr | Lys | Gln | Ile | Ser | Glu | Leu | Asn | Ser | Ile | Asp | Ser | |
| 65 | | | | | 70 | | | | | 75 | | | | | 80 | |
| ACC | ATG | GTC | TAC | TTA | CGC | GGT | AAG | CAT | GAG | TTA | AAT | CAA | TAC | ACC | CCC | 288 |
| Thr | Met | Val | Tyr | Leu | Arg | Gly | Lys | His | Glu | Leu | Asn | Gln | Tyr | Thr | Pro | |
| | | | | 85 | | | | | 90 | | | | | 95 | | |
| TAT | AGC | TTA | CAG | CAA | GCG | CTT | AAA | TTG | CTG | ACT | CAA | TGC | GTT | AAT | ATG | 336 |
| Tyr | Ser | Leu | Gln | Gln | Ala | Leu | Lys | Leu | Leu | Thr | Gln | Cys | Val | Asn | Met | |
| | | | 100 | | | | | 105 | | | | | 110 | | | |
| TCG | CCA | AAC | AGC | ATT | GCG | CCT | TAC | TGT | GCG | CTG | GCA | GAA | TGC | TAC | CTC | 384 |
| Ser | Pro | Asn | Ser | Ile | Ala | Pro | Tyr | Cys | Ala | Leu | Ala | Glu | Cys | Tyr | Leu | |
| | | 115 | | | | | 120 | | | | | 125 | | | | |
| AGC | ATG | GCG | CAA | ATG | GGG | ATT | TTT | GAT | AAA | CAA | AAC | GCA | ATG | ATC | AAA | 432 |
| Ser | Met | Ala | Gln | Met | Gly | Ile | Phe | Asp | Lys | Gln | Asn | Ala | Met | Ile | Lys | |
| | 130 | | | | | 135 | | | | | 140 | | | | | |
| GCT | AAA | GAA | CAT | GCG | ATT | AAG | GCG | ACA | GAG | CTG | GAC | CAC | AAT | AAT | CCA | 480 |
| Ala | Lys | Glu | His | Ala | Ile | Lys | Ala | Thr | Glu | Leu | Asp | His | Asn | Asn | Pro | |
| 145 | | | | | 150 | | | | | 155 | | | | | 160 | |
| CAA | GCT | T | | | | | | | | | | | | | | 487 |
| Gln | Ala | | | | | | | | | | | | | | | |

(2) INFORMATION FOR SEQ ID NO: 2:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO: 2:

| | | | | | | | | | | | | | | |
|---|---|---|---|---|---|---|---|---|---|---|---|---|---|---|
| Gln | Leu | Arg | Pro | Asp | Tyr | Tyr | Ile | Ser | Gly | Gln | Met | Ile | Pro | Asp | Gly |
| 1 | | | | 5 | | | | | 10 | | | | | 15 | |
| Asn | Asp | Asn | Ile | Val | Gln | Ile | Glu | Ile | Val | Arg | Val | Lys | Gly | Tyr | His |
| | | | 20 | | | | | 25 | | | | | 30 | | |
| Leu | Leu | His | Gln | Glu | Ser | Ile | Lys | Leu | Ile | Glu | His | Gln | Pro | Ala | Ser |
| | | 35 | | | | | 40 | | | | | 45 | | | |
| Leu | Leu | Gln | Asn | Lys | Ile | Ala | Asn | Leu | Leu | Leu | Arg | Cys | Ile | Pro | Gly |
| | 50 | | | | | 55 | | | | | 60 | | | | |
| Leu | Arg | Trp | Asp | Thr | Lys | Gln | Ile | Ser | Glu | Leu | Asn | Ser | Ile | Asp | Ser |
| 65 | | | | | 70 | | | | | 75 | | | | | 80 |
| Thr | Met | Val | Tyr | Leu | Arg | Gly | Lys | His | Glu | Leu | Asn | Gln | Tyr | Thr | Pro |
| | | | | 85 | | | | | 90 | | | | | 95 | |
| Tyr | Ser | Leu | Gln | Gln | Ala | Leu | Lys | Leu | Leu | Thr | Gln | Cys | Val | Asn | Met |
| | | | 100 | | | | | 105 | | | | | 110 | | |
| Ser | Pro | Asn | Ser | Ile | Ala | Pro | Tyr | Cys | Ala | Leu | Ala | Glu | Cys | Tyr | Leu |
| | | 115 | | | | | 120 | | | | | 125 | | | |
| Ser | Met | Ala | Gln | Met | Gly | Ile | Phe | Asp | Lys | Gln | Asn | Ala | Met | Ile | Lys |
| | 130 | | | | | 135 | | | | | 140 | | | | |
| Ala | Lys | Glu | His | Ala | Ile | Lys | Ala | Thr | Glu | Leu | Asp | His | Asn | Asn | Pro |
| 145 | | | | | 150 | | | | | 155 | | | | | 160 |
| Gln | Ala | | | | | | | | | | | | | | |

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..17
        (D) OTHER INFORMATION: /standard_name= "SS-1"

(xi) SEQUENCE DESCRIPTION: SEQ ID NO: 3:

GGTCCAGCTC TGTCGCC                       17

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..17
        (D) OTHER INFORMATION: /standard_name= "SS-2"

(xi) SEQUENCE DESCRIPTION: SEQ ID NO: 4:

CCGGGCAGAT GATACCC                       17